United States Patent
Watanabe (10) Patent No.: US 7,421,057 B2
(45) Date of Patent: Sep. 2, 2008

(54) X-RAY CT APPARATUS AND METHOD OF CONTROLLING THE SAME

(75) Inventor: Motoki Watanabe, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 11/561,165

(22) Filed: Nov. 17, 2006

(65) Prior Publication Data

US 2007/0121780 A1    May 31, 2007

(30) Foreign Application Priority Data

Nov. 30, 2005   (JP)   ............... 2005-345546

(51) Int. Cl.
*H05G 1/60*    (2006.01)
(52) U.S. Cl. ............................................. 378/8
(58) Field of Classification Search .............. 378/4, 378/8, 901
See application file for complete search history.

(56) References Cited

U.S. PATENT DOCUMENTS

| | | | |
|---|---|---|---|
| 5,287,276 A | 2/1994 | Crawford et al. | |
| 5,383,231 A | 1/1995 | Yamagishi | |
| 6,243,437 B1 | 6/2001 | Hu et al. | |
| 6,353,653 B1 * | 3/2002 | Edic | 378/8 |
| 6,370,217 B1 * | 4/2002 | Hu et al. | 378/8 |
| 6,504,893 B1 * | 1/2003 | Flohr et al. | 378/8 |
| 6,504,894 B2 | 1/2003 | Pan et al. | |
| 6,560,309 B1 * | 5/2003 | Becker et al. | 378/8 |
| 6,628,743 B1 * | 9/2003 | Drummond et al. | 378/8 |
| 6,708,052 B1 * | 3/2004 | Mao et al. | 600/407 |
| 6,763,082 B2 * | 7/2004 | Ozaki | 378/8 |
| 6,865,250 B2 * | 3/2005 | Londt et al. | 378/8 |
| 7,035,370 B2 | 4/2006 | Flohr et al. | |
| 2002/0118790 A1 * | 8/2002 | Pan et al. | 378/8 |
| 2003/0007593 A1 * | 1/2003 | Heuscher et al. | 378/4 |
| 2004/0082846 A1 | 4/2004 | Johnson et al. | |

FOREIGN PATENT DOCUMENTS

JP    2005-137390    6/2005

* cited by examiner

*Primary Examiner*—Courtney Thomas
*Assistant Examiner*—Alexander H Taningco
(74) *Attorney, Agent, or Firm*—Armstrong Teasdale LLP

(57) ABSTRACT

This invention provides an X-ray CT apparatus capable of addressing a change in heart beats during a scan and a method of controlling the same. The X-ray CT apparatus includes: a data acquisition device for acquiring projection data of a subject by a helical scan synchronized with a heart beat; an image reconstructing apparatus for reconstructing an image on the basis of the collected projection data; and a controller for controlling the data acquisition device and the image reconstructing apparatus. The controller includes: first control means for changing helical pitch in accordance with a change in the heart beat during the helical scan; and second control means for reconstructing images in a plurality of slice positions at equal intervals on the basis of projection data also including projection data collected during the change in the helical pitch.

20 Claims, 10 Drawing Sheets

X-RAY CT APPARATUS AND METHOD OF CONTROLLING THE SAME

CROSS REFERENCE TO RELATED APPLICATIONS

This application claims the benefit of Japanese Application No. 2005-345546 filed Nov. 30, 2005.

BACKGROUND OF THE INVENTION

The present invention relates to an X-ray CT (computed tomography) apparatus and a method of controlling the same. More specifically, the invention relates to an X-ray CT apparatus for acquiring an image of a subject by a helical scan synchronized with a heart beat and to a method of controlling the same.

In the case of imaging heart by an X-ray CT apparatus, a scan is performed while collecting a heart beat signal, and an image is reconstructed by using projection data of an amount of a half scan in a desired heart beat phase. The scan is performed as a helical scan, and a multi-row X-ray detector is used for acquiring projection data. The X-ray CT apparatus using the multi-row X-ray detector is also called an MDCT (Multi Detector Row CT).

Imaging of the heart by an MDCT, the helical pitch is set in accordance with the heart beat so that all of heart beat phases in slice images in a plurality of continuous slice positions become the same and no dropout of projection data occurs between neighboring slice positions (refer to, for example, Japanese Patent Laid-Open No. 2005-137390).

To improve time resolution of image acquisition, projection data of an amount of a half scan is collected in a plurality of heart beats. Image reconstruction based on the projection data collected in such a manner is also called multi-sector reconstruction.

SUMMARY OF THE INVENTION

In the case of performing the helical scan as described above, when the heart beat changes during a scan, the helical pitch becomes asynchronous with the heart beat, so that a high-quality slice image cannot be obtained due to a dropout of data or the like.

An object of the present invention is to realize an X-ray CT apparatus capable of addressing a change in a heart beat during a scan and a method of controlling the same.

The present invention in an aspect for achieving the object provides an X-ray CT apparatus including: a data acquiring device for acquiring projection data of a subject by a helical scan synchronized with a heart beat; an image reconstructing apparatus for reconstructing an image on the basis of the acquired projection data; and a controller for controlling the data acquiring device and the image reconstructing device, and characterized in that the controller includes: first control means for changing helical pitch in accordance with a change in the heart beat during the helical scan; and second control means for reconstructing images in a plurality of slice positions at equal intervals on the basis of projection data also including projection data acquired during a change in the helical pitch.

The present invention in another aspect for achieving the object relates to a method of controlling an X-ray CT apparatus for acquiring projection data of a subject by a helical scan synchronized with a heart beat and reconstructing an image on the basis of the collected projection data, characterized by including the steps of: changing helical pitch in accordance with a change in the heart beat during the helical scan; and reconstructing images in a plurality of slice positions at equal intervals on the basis of projection data also including projection data collected during a change in the helical pitch.

Preferably, the helical pitch is changed by changing relative linear travel speed of an X-ray focal point in the axial direction of the helical scan for the reason that it is sufficient to control only one of two speed components in the circumferential direction and the axial direction.

Preferably, the relative linear travel speed is changed by changing travel speed of a table supporting the subject for the reason that it is easy to control the relative linear travel speed of the X-ray focal point.

Preferably, the data acquisition device acquires two-dimensional projection data since it facilitates reconstruction of images in a plurality of slice positions which are at the equal interval.

Preferably, the data acquisition device acquires projection data via a multi-row X-ray detector because two-dimensional projection data can be easily obtained.

According to the invention in any of the aspects, the X-ray CT apparatus is controlled so that the helical pitch is changed in accordance with a change in the heart beat during a helical scan and images in a plurality of slice positions at equal interval are reconstructed on the basis of projection data also including projection data collected during the change in the helical pitch. Thus, the X-ray CT apparatus capable of addressing a change in the heart beat during a scan and the method of controlling the same can be realized.

DETAILED DESCRIPTION OF THE INVENTION

Figure 1:
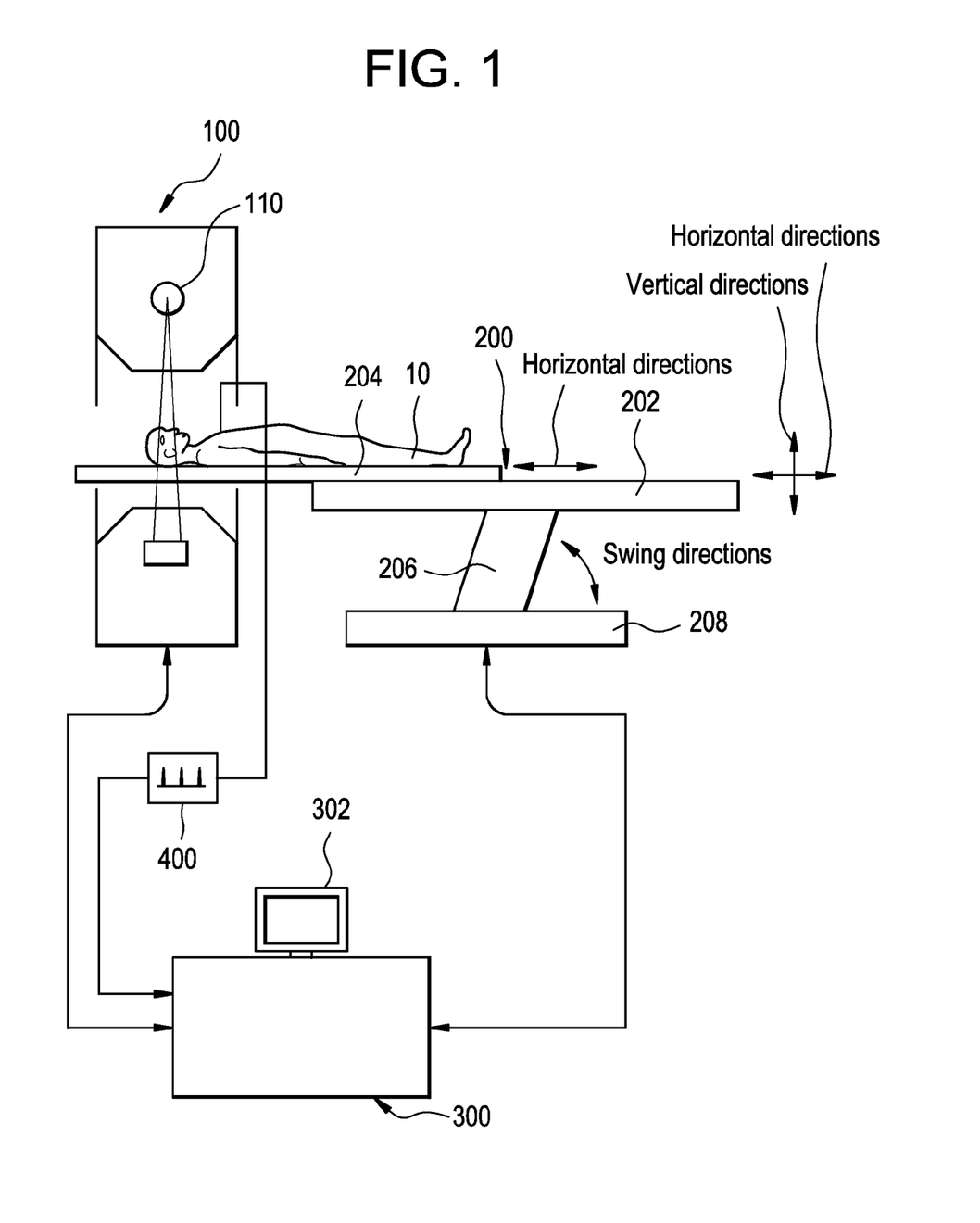
FIG. 1 is a block diagram showing a configuration of an X-ray CT apparatus as an example of the best mode for carrying out the present invention.

Best modes for carrying out the present invention will be described below with reference to the appended drawings. The present invention, however, is not limited to the best modes for carrying out the invention. FIG. 1 schematically shows the configuration of an X-ray CT apparatus. The apparatus is an example of the best mode for carrying out the invention. With the configuration of the apparatus, an example of the best mode for carrying out the invention related to the X-ray CT apparatus will be described. By the operation of the apparatus, an example of the best mode for carrying out the invention related to a method of controlling the X-ray CT apparatus will be described.

As shown in FIG. 1, the apparatus has a gantry 100, a table 200, an operator console 300, and an electrocardiograph 400. The gantry 100 scans a subject 10 loaded by the table 200 by an X-ray irradiating/detecting apparatus 110 and acquires projection data of a plurality of views. The scan is performed by rotating the X-ray irradiating/detecting apparatus 110 in the gantry 100. Herein below, the rotation of the X-ray irradiating/detecting apparatus 110 will be also called rotation of the gantry 100.

The projection data collected by the gantry 100 is input to the operator console 300. To the operator console 300, a heart beat signal is also input via the electrocardiograph 400. The operator console 300 has therein a data processor such as a computer and stores input data and a heart beat signal into a memory. The operator console 300 performs image reconstruction on the basis of the projection data and the heart beat signal. The operator console 300 is an example of the image reconstructing apparatus in the present invention.

The image reconstruction is performed by using projection data of an amount of a half scan in a predetermined heart beat phase. The projection data of the amount of the half scan is data collected in one heart beat or data in a plurality of heart beats. The reconstructed image is displayed on a display 302.

The operator console 300 controls the gantry 100 and the table 200. Under control of the operator console 300, the gantry 100 performs a scan with predetermined parameters, and the table 200 performs positioning of the subject 10 in an image acquisition space so that a predetermined region is scanned. Position information of the table 200 is fed back to the operator console 300. The operator console 300 is an example of the controller in the present invention.

The subject 10 is positioned by adjusting height of a top plate 202 and horizontal travel distance of a cradle 204 on the top plate 202 by a position adjusting mechanism which is internally provided. The height of the top plate 202 is adjusted by swinging a support 206 around the portion attached to a base 208 as a center.

By performing a scan in a state where the cradle 204 is stopped, an axial scan is performed. By performing a scan while continuously moving the cradle 204, a helical scan is performed. The gantry 100 and the table 200 are an example of the data acquisition device in the present invention.

In the case of a structure in which the gantry 100 can move linearly along the table 200, a helical scan may be performed by linearly moving the gantry 100 in place of the cradle 204.

In short, the linear travel in the axial direction of the helical scan may be relative travel between the gantry 100 and the table 200. Although an example of moving the cradle 204 will be described herein below, the case of moving the gantry 100 is similar to the example.

Figure 2:
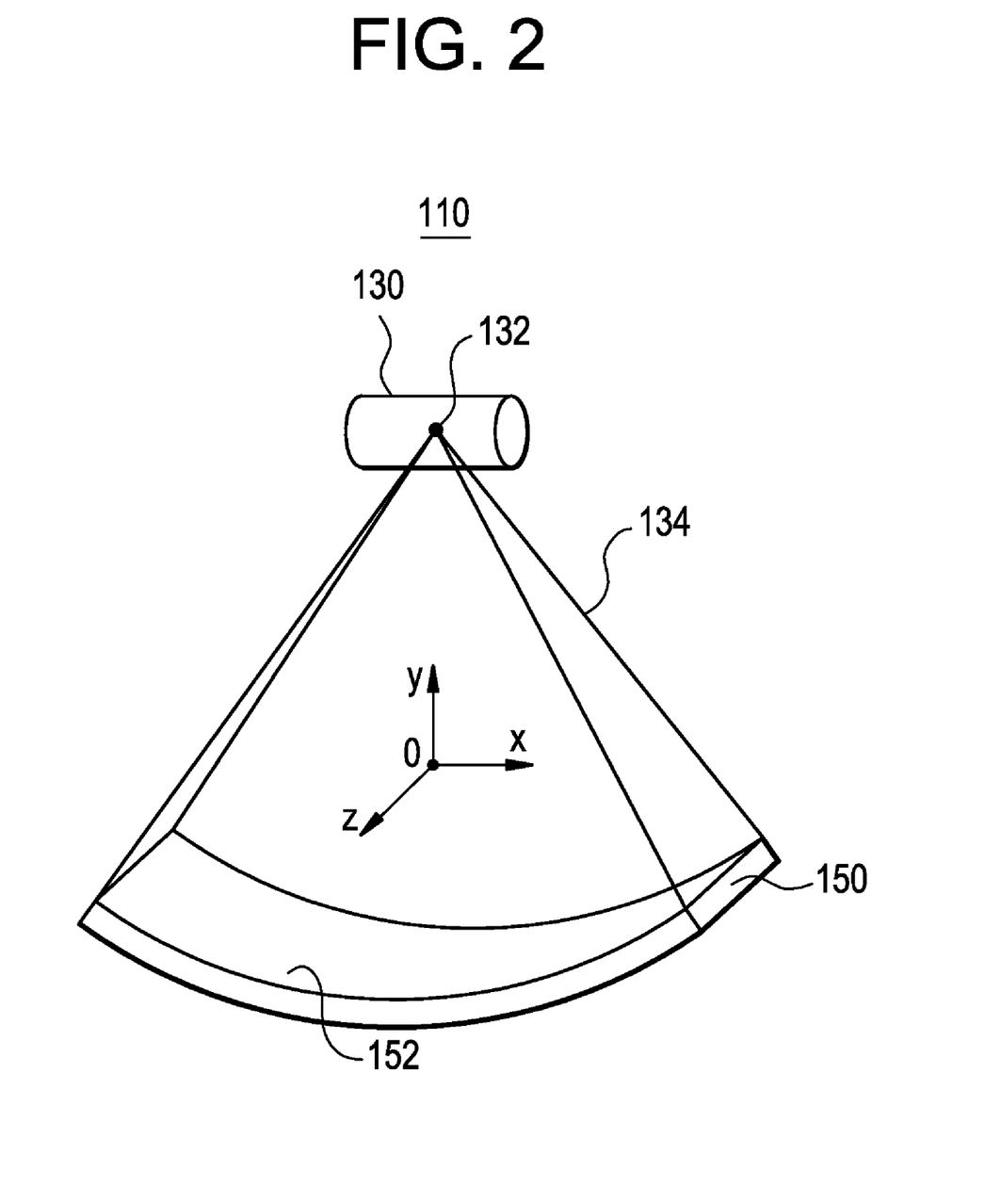
FIG. 2 is a diagram showing the configuration of an X-ray irradiating/detecting apparatus in the X-ray CT apparatus as an example of the best mode for carrying out the present invention.

FIG. 2 schematically shows the configuration of the X-ray irradiating/detecting apparatus 110. The X-ray irradiating/detecting apparatus 110 detects an X-ray 134 emitted from a focal point 132 of an X-ray tube 130 by an X-ray detector 150.

The X-ray 134 is formed as a cone beam X-ray by a not-shown collimator. The X-ray detector 150 has an X-ray entrance plane 152 which spreads two-dimensionally in correspondence with spread of the cone beam X-ray. The X-ray entrance plane 152 is curved so as to construct part of a cylinder. The center axis of the cylinder passes through the focal point 132.

The X-ray irradiating/detecting apparatus 110 rotates around the center axis passing through the image acquisition center, that is, isocenter O. The center axis is parallel with the center axis of a partial cylinder formed by the X-ray detector 150.

The direction of the center axis of rotation is set as a z direction, the direction connecting the isocenter O and the focal point 132 is set as a y direction, and a direction perpendicular to the z direction and the y direction is set as an x direction. The x, y, and z axes are three axes of a rectangular coordinate system using the z axis as a center axis. The z axis is also the axis of a helical scan.

Figure 3:
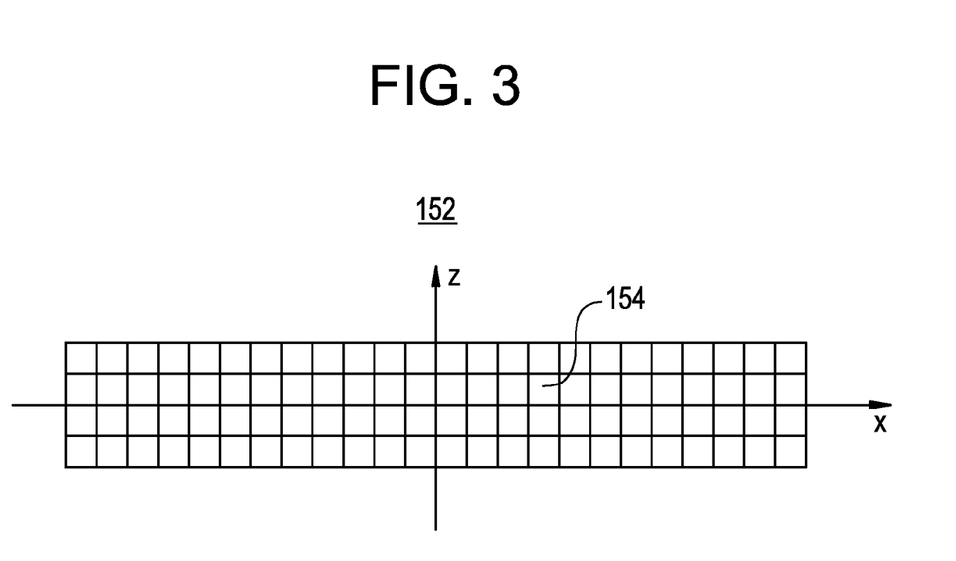
FIG. 3 is a diagram showing the configuration of an X-ray entrance plane of an X-ray detector in the X-ray CT apparatus as an example of the best mode for carrying out the present invention.

FIG. 3 is a schematic plan view of the X-ray entrance plane 152 of the X-ray detector 150. In the X-ray entrance plane 152, detection cells 154 are arranged two-dimensionally in the x and y directions. That is, the X-ray entrance plane 152 is a two-dimensional array of the detection cells 154.

Each of the detection cells 154 serves as a detection channel in the X-ray detector 150. Consequently, the X-ray detector 150 takes the form of a multi-channel X-ray detector. The detection cell 154 is constructed by, for example, combination of a scintillator and a photo diode.

Such an X-ray detector 150 is also called a multi-row X-ray detector using the x direction as a channel direction and using the z direction as a column direction. The number of channels is, for example, 1,024 and the number of columns is, for example, 64. By using a multi-row X-ray detector as the X-ray detector 150, two-dimensional projection data can be acquired at once and an efficient scan can be performed.

Figure 4:
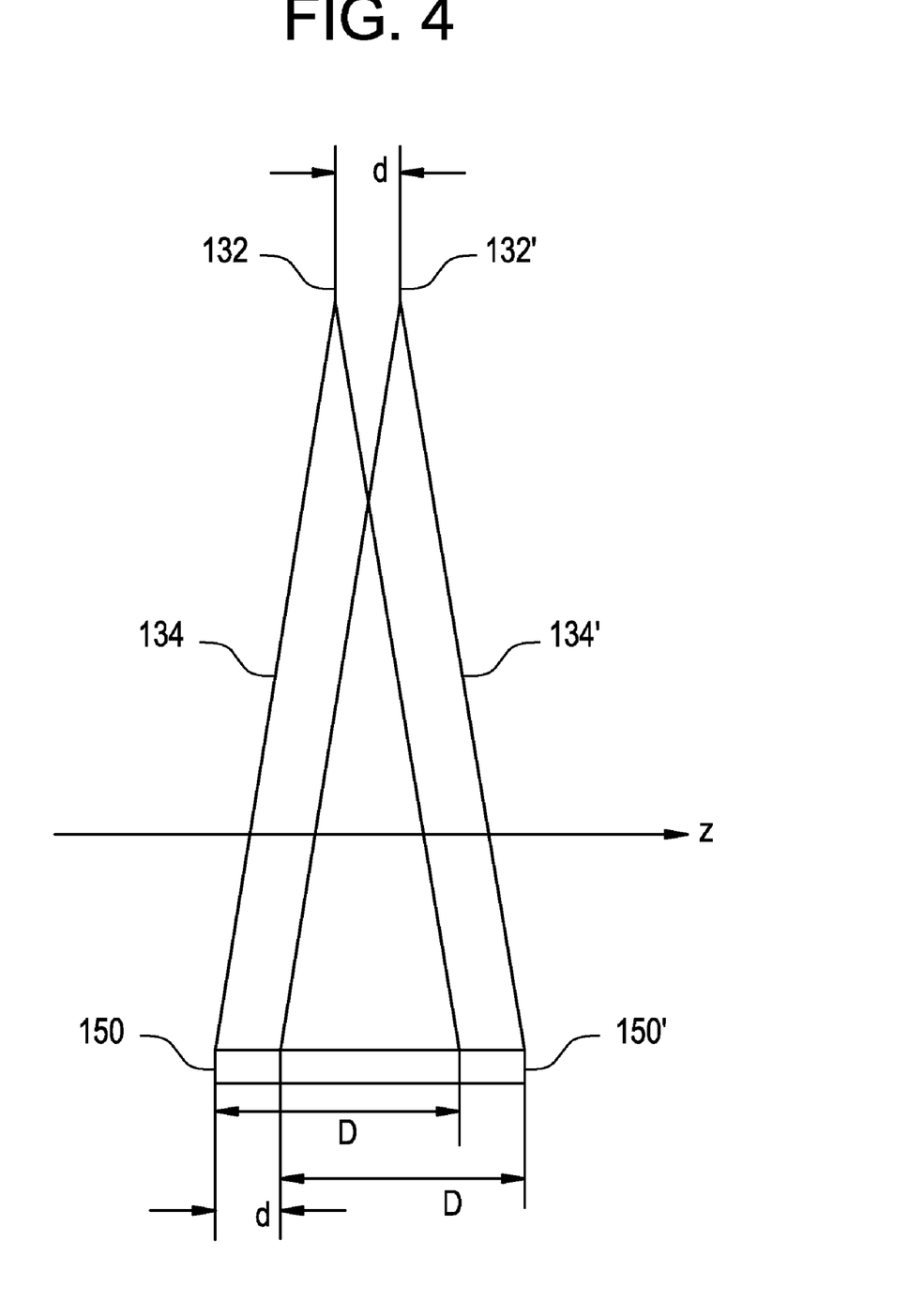
FIG. 4 is a diagram showing the concept of a helical pitch.

FIG. 4 shows the concept of the helical pitch. FIG. 4 shows a state where the X-ray focal point 132 moves in the z axis direction only by distance "d" in one rotation of the helical scan. The distance "d" is relative linear travel distance between the gantry 100 and the table 200. The helical pitch is given as a value obtained by normalizing the distance "d" with the width D in the z axis direction of the X-ray detector 150. That is, the helical pitch is given as d/D.

Figure 5:
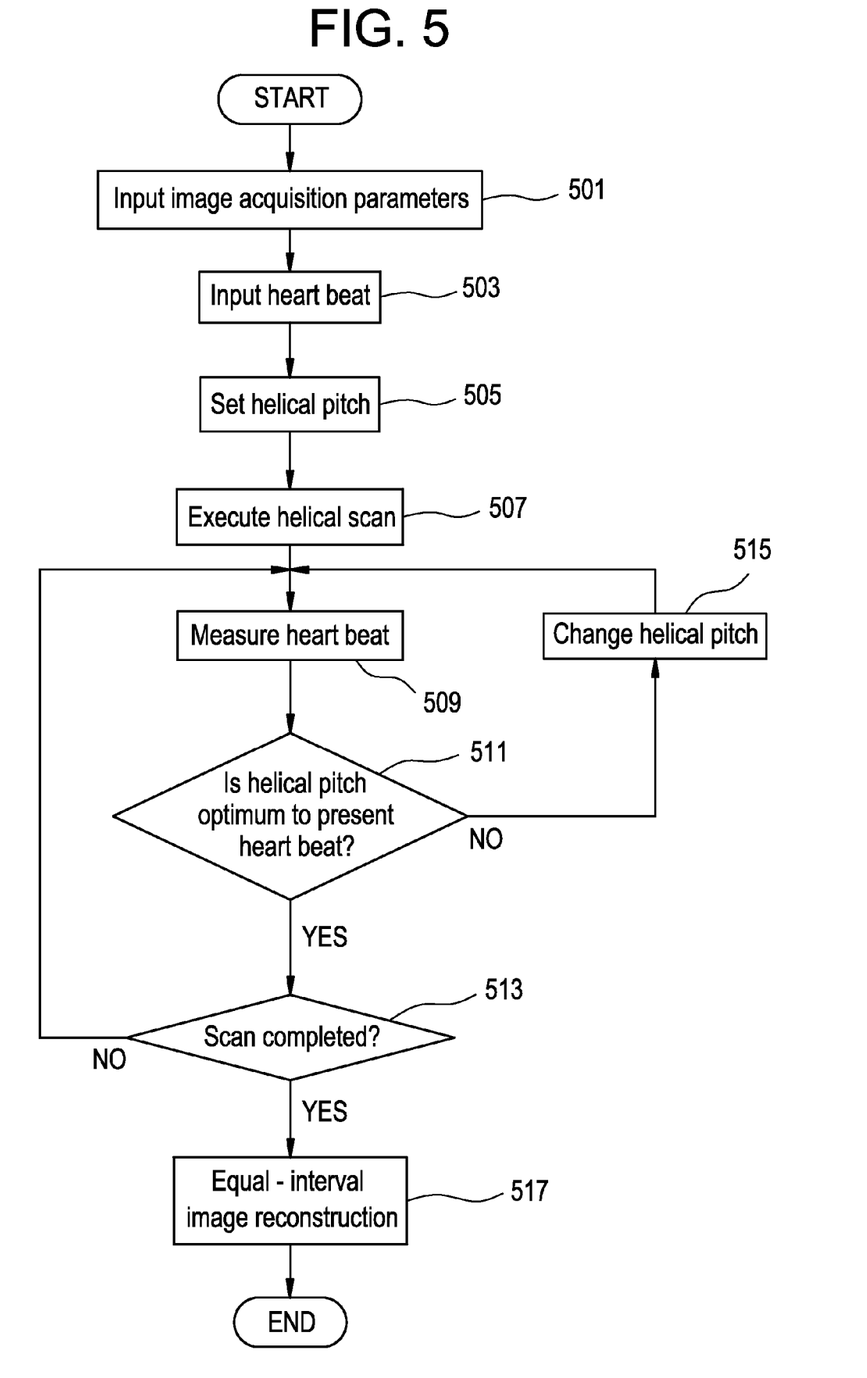
FIG. 5 is a flowchart showing an example of operation of the X-ray CT apparatus as an example of the best mode for carrying out the invention.

The operation of the apparatus will be described. FIG. 5 shows the flow chart of the operation of the apparatus. As shown in FIG. 5, in step 501, image acquisition parameters are input. The image acquisition parameters are input by operation of the operator console 300 by the operator. By the operation, X-ray tube voltage, X-ray tube current, gantry rotation speed, scan start and end positions, heart beat phase of image acquisition, image reconstruction parameters, and the like are input.

In step 503, a heart beat is input. The heart beat is displayed on the display 302 on the basis of input signals from the electrocardiograph 400, and the operator inputs the heart beat in accordance with the display. The heart beat is expressed by, for example, heart rate. Alternatively, the heart beat may be also expressed by a cardiac cycle. There is an inverse relationship between the heart rate and the cardiac cycle. Although the case paying attention to the heart rate will be described herein below, in the case of paying attention to the cardiac cycle, it is sufficient to use the inverse of the heart rate.

In step 505, the helical pitch is set. The helical pitch is automatically set by the operator console 300 interlockingly with the input of the heart rate. The operator console 300 pre-stores the correspondences between the heart rate and the optimum helical pitch and, on the basis of the correspondences, sets the helical pitch.

Figure 6A:
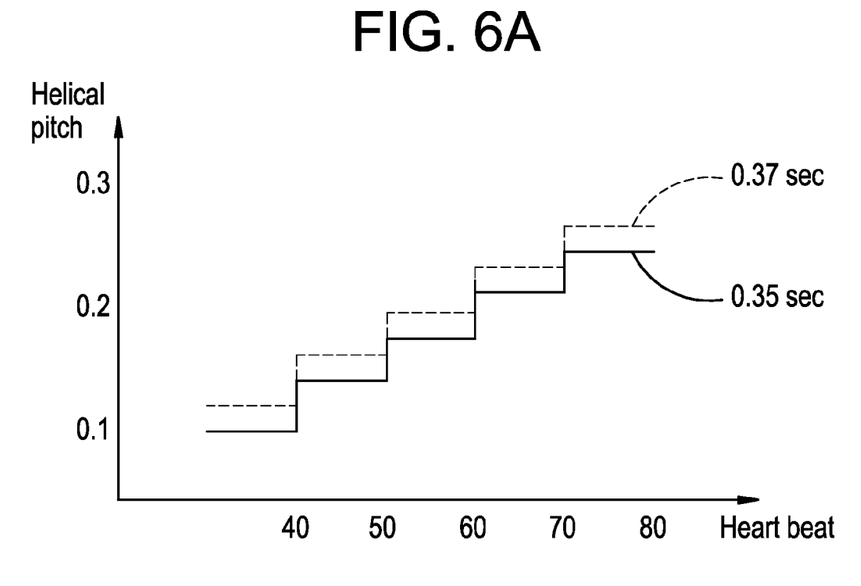
FIGS. 6a and 6b are flowcharts showing correspondences between heart beats and the optical helical pitch.
Figure 6B:
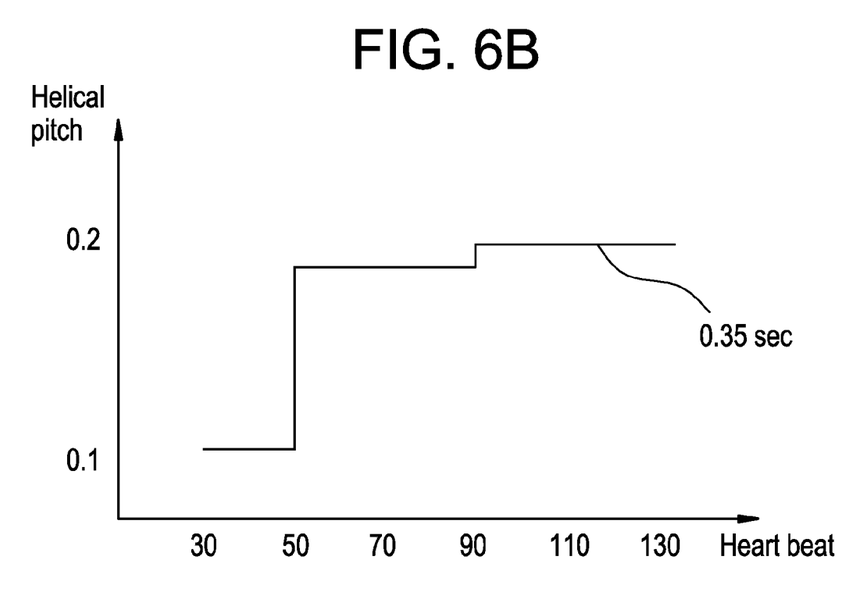

The correspondences between the heart beat and the optimum helical pitch are, for example, as shown in FIGS. 6A and 6B. Such correspondences are determined by induction from past image acquisition records, or the like. FIG. 6A shows the case where projection data of the amount of a half scan is collected in one heart beat. FIG. 6B shows the case where the projection data of the amount of the half scan is collected in two heart beats. As shown in FIGS. 6A and 6B, the higher the heart beat is, the higher the optimum helical pitch is.

The optimum helical pitch with respect to the same heart beat varies according to the gantry rotation speed. Consequently, there is a plurality of correspondences using the gantry rotation speed as a parameter. In FIGS. 6A and 6B, the gantry rotation speed is expressed as rotation time per rotation. Such correspondences are stored as a mathematical table or numerical expression in a memory.

In step 507, a helical scan is executed. The helical scan starts from the scan start position and projection data is collected. The helical scan is performed in a state where the patient holds his/her breath.

The helical scan is performed at the optimum helical pitch. Specifically, the travel speed of the cradle 204 on which the subject 10 is placed is controlled so as to be speed corresponding to the optimum helical pitch. In the specification, the travel speed of the cradle 204 is also called table travel speed. When the cradle is fixed and the gantry moves, the gantry travel speed is controlled.

In step 509, heart beat measurement is conducted. The heart beat is measured in parallel with the helical scan. By the operation, the present value of the heart beat during the helical scan is obtained.

In step 511, whether the helical pitch is optimum to the present heart beat or not is determined. For the determination, the correspondences shown in FIGS. 6A and 6B are used.

When the helical pitch is determined to be optimum, in step 513, whether the scan has completed or not is determined. When the helical scan reaches the scan end position, the scan completes. If not, it is determined that the scan has not completed, and the apparatus returns to step 509 and measures the heart beat. During the determination, the helical scan continues.

During the period in which the helical pitch is optimum to the present heart beat and the scan has not completed, the operations in steps 509 to 513 are repeated. In such a manner, the scan continues at the helical pitch initially set.

The heart beat often changes during the scan. When the heart beat changes, the helical pitch initially set changes from the optimum value. In such a case, it is determined in step 511 that the helical pitch is not optimum to the present heart beat.

Based on the determination, the helical pitch is changed in step 515. The helical pitch is changed by specifying the helical pitch optimum to the present value of the heart beat from the correspondences shown in FIGS. 6A and 6B and controlling the table speed so that the helical pitch becomes the optimum helical pitch.

By the operation, the helical scan is performed at the new helical pitch. The helical pitch is changed under control of the operator console 300. The operator console 300 for controlling a change in the helical pitch is an example of first control means in the present invention.

Preferably, the operation loop of steps 509, 511, and 515 is repeated in shorter time cycles as the heart beat becomes higher so that the apparatus can address a change in the heart beat at high speed.

Figure 7:
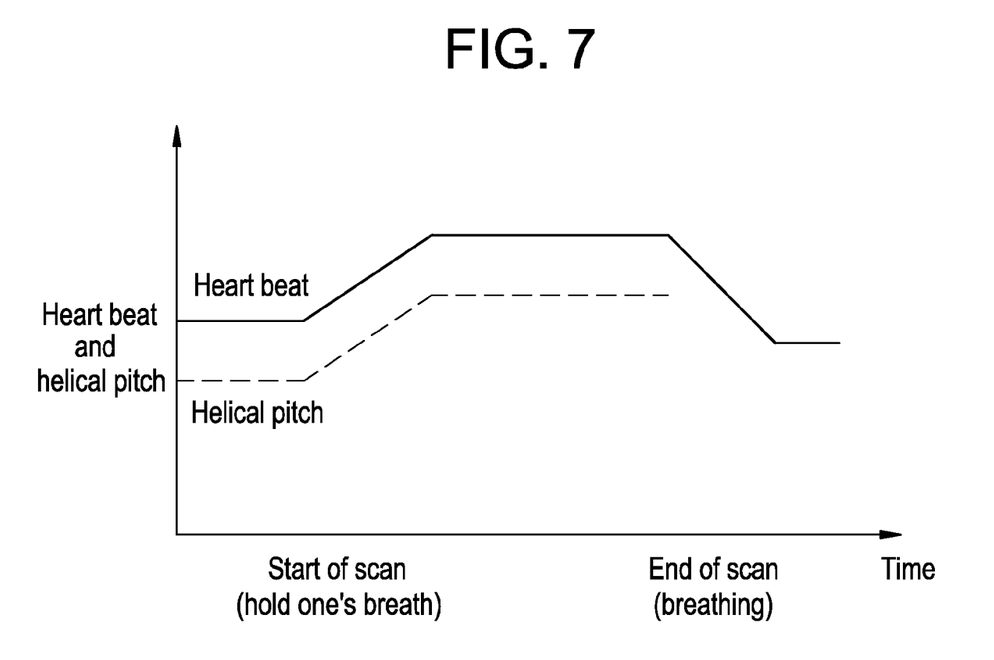
FIG. 7 is a diagram showing an example of a change in the helical pitch in response to a change in the heart beat.

FIG. 7 shows an example of a change in the helical pitch corresponding to a change in the heart beat. In FIG. 7, the transition with time of the heart beat is expressed by a solid-line graph and the transition of the helical pitch corresponding to the transition with time of the heart beat is expressed by a broken-line graph.

The scan is performed during the patient holds his/her breath. The heart beat often changes when the patient starts holding his/her breath. The helical pitch changes so as to follow the heart beat. Projection data is collected also during such a change in the helical pitch.

At this time, the X-ray tube current may be increased/decreased in accordance with increase/decrease of the helical pitch. Consequently, the X-ray exposure dose of the subject 10 can be made constant irrespective of the helical pitch for the reason that larger X-ray tube current has to be supplied as the helical pitch increases.

When the helical scan reaches the scan end position, completion of the scan is determined in step 513, and equal-interval image reconstruction is performed in step 517. The equal-interval image reconstruction is performed on the basis of the image reconstruction parameters which are input in step 501.

The equal-interval image reconstruction is performed by also using projection data collected during a change in the helical pitch. For the equal-interval image reconstruction using also projection data collected during a change in the helical pitch, the technique of known variable pitch reconstruction disclosed in Japanese Patent Laid-Open No. 2005-40582 is used.

The point of the technique is that also when the helical pitch continuously changes due to acceleration/deceleration of the table, the X-ray transmission direction in each of a plurality of image reconstruction positions which are set at equal intervals is obtained on the basis of each of instantaneous values of the table position coordinates, and image reconstruction is performed by using projection data adapted to the X-ray transmission direction.

Figure 8:
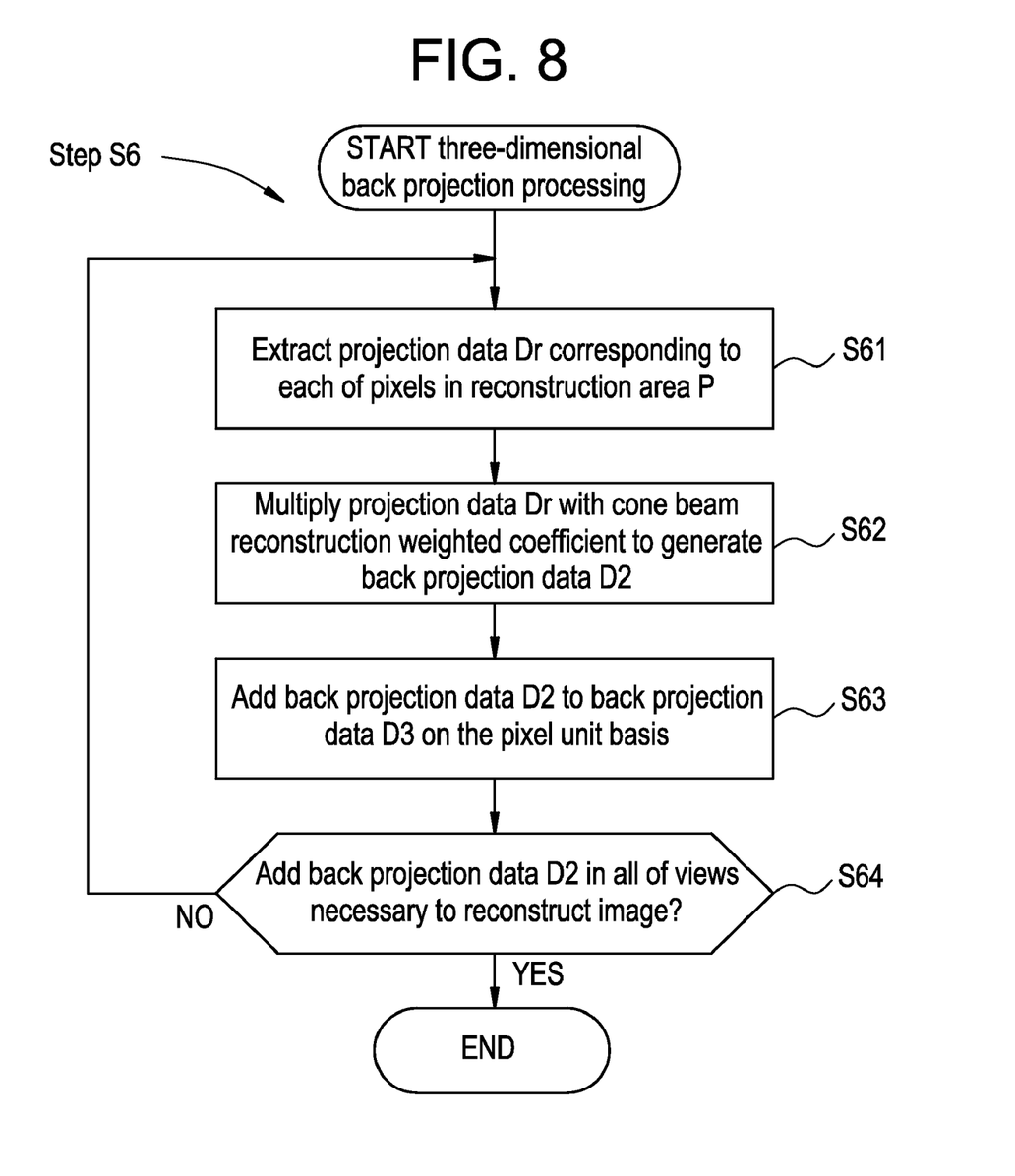
FIG. 8 is a flowchart of a three-dimensional back projection process as a main part of image reconstruction.

FIG. 8 is a flowchart showing the details of a three-dimensional back projection process as a main part of the image reconstruction.

An image is reconstructed as a three-dimensional image in an xy plane perpendicular to the z axis. A reconstruction plane P is parallel with the xy plane.

In step S61, attention is paid to one of all of views (that is, for example, views of the half scan) necessary for reconstructing a slice image, and projection data Dr corresponding to each of pixels in the reconstruction area P is extracted.

Figure 9A:
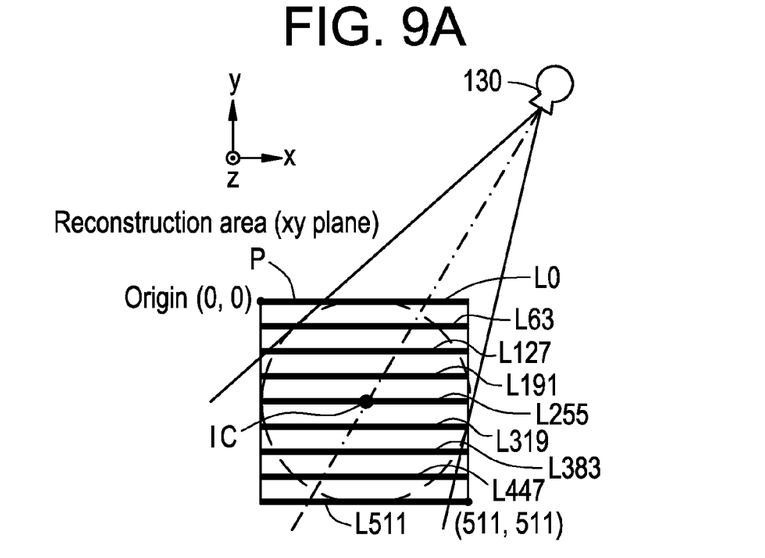
FIGS. 9a and 9b are diagrams showing the geometrical relation between an image reconstruction area and an X ray passing through the image reconstruction area.
Figure 9B:
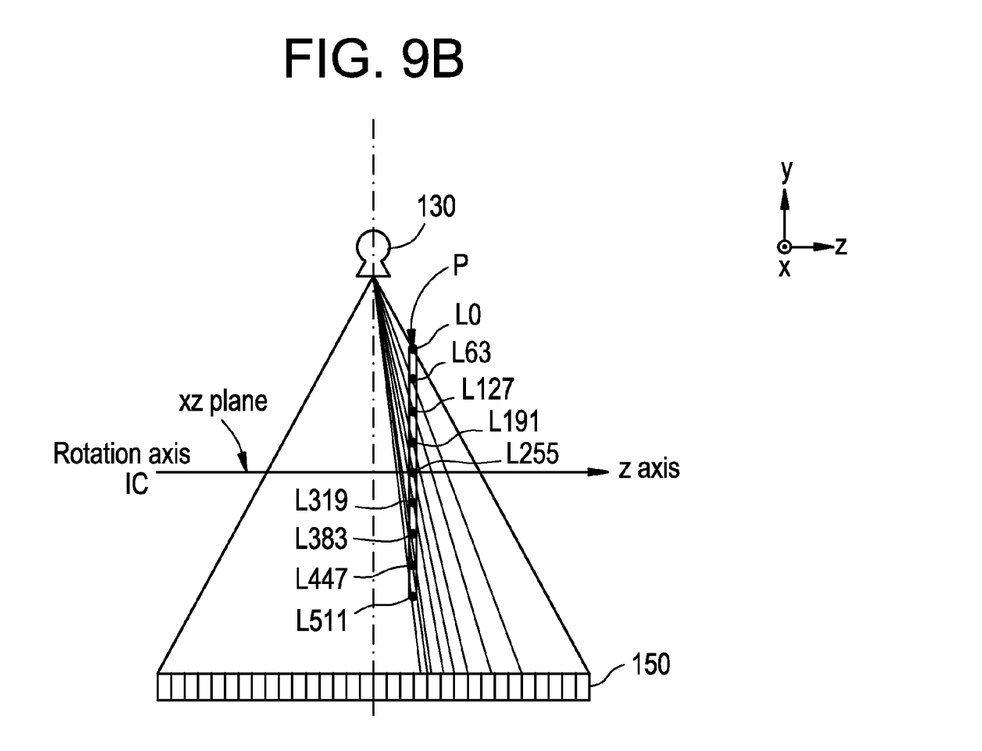
Figure 10:
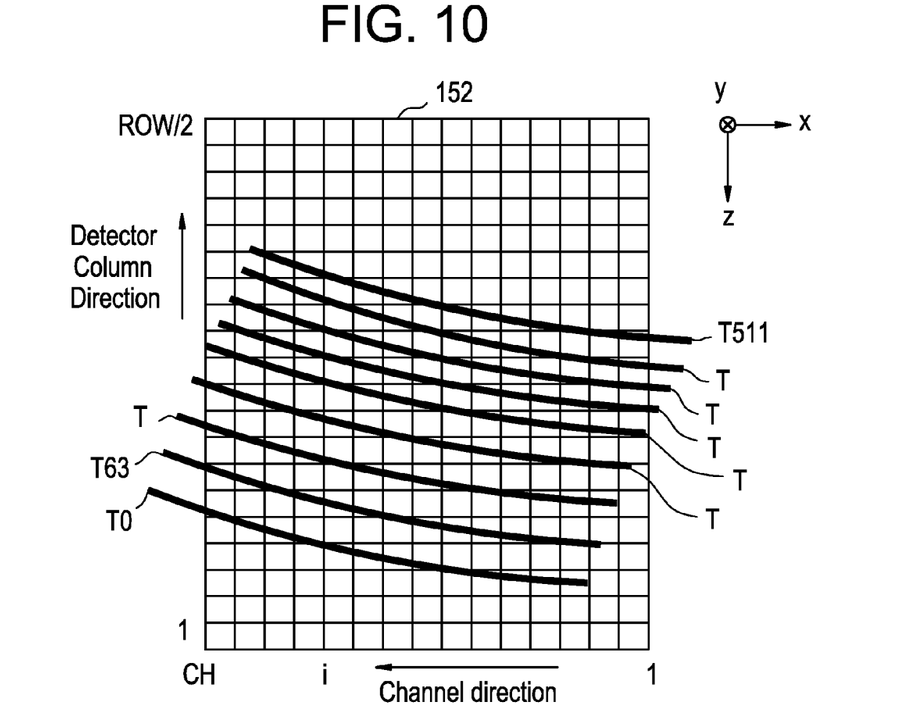
FIG. 10 is a diagram showing an image reconstruction area projected to the X-ray entrance plane of the X-ray detector.

As shown in FIGS. 9A and 9B, a square region of 512×512 pixels parallel to the xy plane is set as the reconstruction area P. Pixel line L0 at y=0, pixel line L63 at y=63, pixel line L127 at y=127, pixel line L191 at y=191, pixel line L255 at y=255, pixel line L319 at y=319, pixel L383 at y=383, pixel line L447 at y=447, and pixel line L511 at y=511 which are parallel to the x axis of y=0 are used as an example. By extracting projection data on lines T0 to T511 as shown in FIG. 10 obtained by projecting the pixel lines L0 to L511 onto the plane of the multi-slice X-ray detector 150 in the X-ray transmission direction, the extracted data is used as projection data Dr (view, x, y) in the pixel lines L0 to L511. Here, x, y correspond to the pixels (x, y) of a slice image.

The X-ray transmission direction is determined by geometric positions among the X-ray focal point of the X-ray tube 130, each pixel, and the multi-row X-ray detector 150. Since a z coordinate z (view) of X-ray detector data D0 (view, j, i) is attached as a table linear travel z-direction position Ztable (view) to the X-ray detector data and is known, the X-ray focal point and the X-ray transmission direction in a data collection geometric system of the multi-row X-ray detector can be obtained accurately from the X-ray detector data D0 (view, j, i) during acceleration/deceleration.

In the case where part of a line extends to the outside in the channel direction of the multi-row X-ray detector 150 like a line T0 obtained by projecting the pixel line L0 to the plane of the multi-row X-ray detector 150 in the X-ray transmission direction, the corresponding projection data Dr (view, x, y) is set to "0". In the case where the line extends to the outside in the z direction, the projection data Dr (view, x, y) is obtained by extrapolation.

Figure 11:
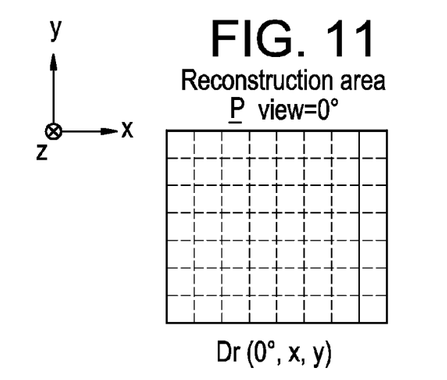
FIG. 11 is a diagram showing arrangement of data Dr in the image reconstruction area.

As described above, as shown in FIG. 11, the projection data Dr (view, x, y) corresponding to each of the pixels in the reconstruction area P can be extracted.

Figure 12:
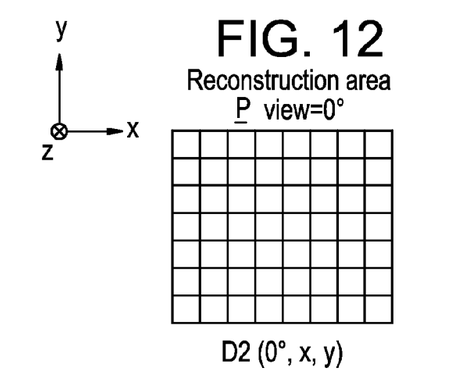
FIG. 12 is a diagram showing arrangement of data D2 in the image reconstruction area.

Referring again to FIG. 8, in step S62, the projection data Dr (view, x, y) is multiplied with a cone beam reconstruction weighted coefficient, thereby generating projection data D2 (view, x, y) as shown in FIG. 12.

The cone beam reconstruction weighted coefficient w (i, j) is as follows. In the case of fan beam image reconstruction, generally, when the angle formed between a straight line connecting the focal point of the X-ray tube 130 and a pixel g (x, y) on the reconstruction area P (on the xy plane) at view=$\beta a$ and a center axis Bc of an X-ray beam is $\gamma$ and the opposed view is view=$62\ b$, the following expression is obtained.

$$\beta b = \beta a + 180° - 2\gamma \quad \text{Equation 1}$$

When the angle formed between an X-ray beam passing through the pixel g (x, y) on the reconstruction area P and the reconstruction plane P is $\alpha a$ and the angle formed between an X-ray beam opposed to the above-described X-ray beam and the reconstruction plane P is $\alpha b$, the angles $\alpha a$ and $\alpha b$ are multiplied with cone beam reconstruction weighted coefficients $\omega a$ and $\omega b$ depending on the angles and the resultants are added, thereby obtaining back projection pixel data D2 (0, x, y). In this case, the following expression is obtained.

$$D2(0, x, y) = \omega a \cdot D2(0, x, y)_{13} a + \omega b \cdot D2(0, x, y)\_b \quad \text{Equation 2}$$

where D2(0, x, y)_a denotes back projection data of the view $\beta a$ and D2(0, x, y)_b denotes back projection data of the view $\beta b$ The sum of the opposed beams of the cone beam reconstruction weighted coefficients is expressed as follows.

$$\omega a + \omega b = 1 \quad \text{Equation 3}$$

By performing multiplication with the cone beam reconstruction weighted coefficients $\omega a$ and $\omega b$ and addition, a cone angle artifact can be reduced.

For example, the cone beam reconstruction weighted coefficients $\omega a$ and $\omega b$ calculated by the following equations can be used. Here, ga denotes a weighted coefficient of the view $\beta a$ and gb denotes a weighted coefficient of the view $\beta b$.

When ½ of the fan beam angle is set as $\gamma max$, the following expressions are obtained.

$$ga = f(\gamma max, \alpha a, \beta a)$$

$$gb = f(\gamma max, \alpha b, \beta b)$$

$$xa = 2 \cdot ga^q / (ga^q + gb^q)$$

$$xb = 2 \cdot gb^q / (ga^q + gb^q)$$

$$wa = xa^2 \cdot (3 - 2xa)$$

$$wb = xb^2 \cdot (3 - 2xb) \quad \text{Equation 4}$$

(for example, q=1)

For example, when max[ ] is a function of taking a larger value, as an example of ga and gb, the following is obtained.

$$ga = \max[0, \{(\pi/2 + \gamma max) - |\beta a|\}] \cdot |\tan(\alpha a)|$$

$$gb = \max[0, \{(\pi/2 + \gamma max) - |\beta b|\}] \cdot |\tan(\alpha b)| \quad \text{Equation 5}$$

In the case of the fan beam image reconstruction, further, each of pixels on the reconstruction area P is multiplied with the distance coefficient. The distance coefficient is expressed as $(r1/r0)^2$ when the distance from the focal point of the X-ray tube 130 to the detector column j of the multi-row X-ray detector 150 corresponding to the projection data Dr and the channel i is r0 and the distance from the focal point of the X-ray tube 130 to a pixel on the reconstruction area P corresponding to the projection data Dr is r1.

Figure 13:
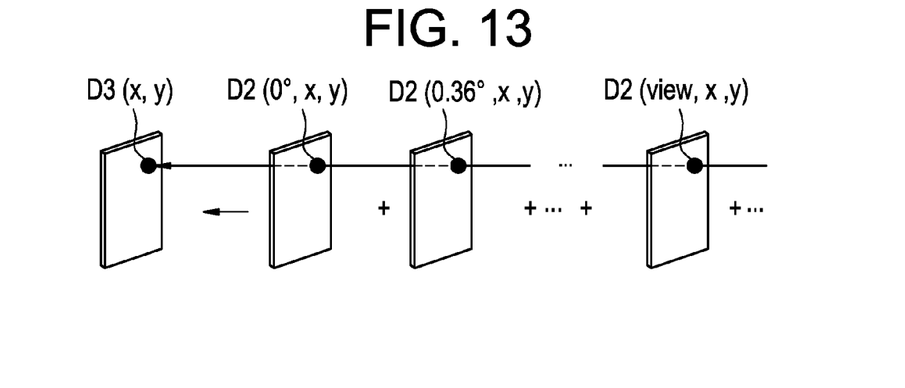
FIG. 13 is a diagram showing addition of the data D2 in the image reconstruction area.

In step S63, as shown in FIG. 13, the projection data D2 (view, x, y) is added to the back projection data D3(x, y) which is cleared in advance in a pixel correspondence manner.

In step S64, the steps S61 to S63 are repeated with respect to all of the views necessary to reconstruct a slice image (that is, for example, views of the amount of a half scan) and, as shown in FIG. 13, back projection data D3(x, y) is obtained.

By performing the three-dimensional back projection using two-dimensional projection data as described above, a plurality of reconstructed images at equal intervals can be obtained irrespective of a change in the helical pitch during a scan. Since the helical pitch is dynamically optimized so as to follow a change in the heart beat, the heart beat phases of a plurality of images become the same and, moreover, no dropout of data occurs.

The equal-interval image reconstruction is performed under control of the operator console 300. The operator console 30 controlling the equal-interval image reconstruction is an example of second control means in the present invention.

In the apparatus, the helical pitch is changed by changing the relative linear travel speed of the X-ray focal point in the axial direction of a helical scan. Consequently, it is sufficient to control only one of two speed components in the circumferential direction and the axial direction of the helical scan.

Since the relative linear travel speed is changed by changing the moving speed of the table that supports the subject, it is easy to control the relative linear travel speed of the X-ray focal point.

The invention claimed is:

1. An X-ray CT apparatus comprising:
    a data acquisition device for acquiring projection data of a subject by a helical scan synchronized with a heart beat;
    an image reconstructing device for reconstructing an image on the basis of the acquired projection data; and
    a controller for controlling the data acquisition device and the image reconstructing device,
    wherein the controller comprises:
    a first control device for changing helical pitch in accordance with a change in the heart beat during the helical scan; and
    a second control device for reconstructing images in a plurality of slice positions at equal intervals on the basis of projection data also including projection data acquired during the change in the helical pitch.

2. The X-ray CT apparatus according to claim 1, wherein the helical pitch is changed by changing relative linear travel speed of an X-ray focal point in the axial direction of the helical scan.

3. The X-ray CT apparatus according to claim 2, wherein the relative linear travel speed is changed by changing travel speed of a table supporting the subject.

4. The X-ray CT apparatus according to claim 1, wherein the data acquisition device acquires two-dimensional projection data.

5. The X-ray CT apparatus according to claim 1, wherein the data acquisition device acquires projection data via a multi-row X-ray detector.

6. A method of controlling an X-ray CT apparatus, for controlling an X-ray CT apparatus for acquiring projection data of a subject by a helical scan synchronized with a heart beat and reconstructing an image on the basis of the collected projection data, comprising the steps of:
    changing helical pitch in accordance with a change in the heart beat during the helical scan; and
    reconstructing images in a plurality of slice positions at equal intervals on the basis of projection data also including projection data acquired during a change in the helical pitch.

7. The method of controlling an X-ray CT apparatus according to claim 6, wherein the helical pitch is changed by changing relative linear travel speed of an X-ray focal point in the axial direction of the helical scan.

8. The method of controlling an X-ray CT apparatus according to claim 7, wherein the relative linear travel speed is changed by changing travel speed of a table supporting the subject.

9. A method of imaging an subject using a Computed Tomography (CT) imaging apparatus, said method comprising:
    scanning a patient using the CT imaging apparatus;
    determining at least one of a heart rate and a cardiac cycle of the subject while the subject is being scanned;
    automatically changing a helical pitch of the CT imaging apparatus during the subject scanning based on the determined heart rate or cardiac cycle; and
    reconstructing at least one image of the subject.

10. A method in accordance with claim 9, further comprising entering at least one image acquisition parameter into the CT imaging apparatus prior to scanning the subject.

11. A method in accordance with claim 10, further comprising entering at least one of a X-ray tube voltage, a X-ray tube current, a gantry rotation speed, a scan start position, a scan end position, and a heart beat phase into the CT imaging apparatus.

12. A method in accordance with claim 9, further comprising increasing or decreasing the helical pitch of the CT imaging apparatus based on a corresponding increase or decrease in the heart rate of the subject.

13. A method in accordance with claim 12, further comprising:
    positioning the subject on a cradle; and
    controlling the travel speed of the cradle based on the helical pitch while scanning the subject.

14. A method in accordance with claim 13, further comprising:
    measuring at least one of the heart rate and cardiac cycle of the subject while scanning the subject; and
    calculating an optimal helical pitch based on the measured heart rate.

15. A method in accordance with claim 14, further comprising modifying a travel speed of the cradle based on the optimal helical pitch.

16. A method in accordance with claim 14, further comprising modifying a relative linear travel speed of an X-ray focal point in an axial direction of the helical scan to change the helical pitch.

17. A method in accordance with claim 16, further comprising adjusting an X-ray tube current based on the optimal helical pitch.

18. A method in accordance with claim 17, further comprising adjusting an X-ray tube current based on the optimal helical pitch such that an X-ray dosage absorbed by a patient is substantially constant during the scanning.

19. A method in accordance with claim 18, further comprising reconstructing an image of the subject in a plurality of slice positions at equal intervals on the basis of projection data acquired during a change in the helical pitch.

20. A method in accordance with claim 19, further comprising reconstructing a three-dimensional image of the subject.

* * * * *